US00PP32854P3

(12) United States Plant Patent
Scorza

(10) Patent No.: US PP32,854 P3
(45) Date of Patent: Mar. 2, 2021

(54) RED LEAF PEACH ROOTSTOCK NAMED 'JAM 23'

(50) Latin Name: ***Prunus persica* (L.) Batsch**
Varietal Denomination: JAM 23

(71) Applicant: The United States of America, as represented by the Secretary of Agriculture, Washington, DC (US)

(72) Inventor: Ralph Scorza, Sheperdstown, WV (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 274 days.

(21) Appl. No.: 15/732,076

(22) Filed: Sep. 13, 2017

(65) Prior Publication Data

US 2019/0082570 P1 Mar. 14, 2019

(51) Int. Cl.
*A01H 5/08* (2018.01)
*A01H 6/74* (2018.01)

(52) U.S. Cl.
USPC ..... Plt./194
CPC ..... *A01H 6/7463* (2018.05)

(58) Field of Classification Search
USPC ..... Plt./194
CPC ..... A01H 6/7463
See application file for complete search history.

*Primary Examiner* — Anne Marie Grunberg
(74) *Attorney, Agent, or Firm* — John Fado; Ariel Atkinson

(57) ABSTRACT

This invention relates to new and distinct cultivar of peach rootstock tree named 'Jam 23'. The new cultivar is primarily characterized by its cold hardiness and late blooming making it suitable for the reliable production of rootstock seeds with red leaf color, high levels of germination and cold hardiness.

12 Drawing Sheets

Latin name of the genus and species of the plant claimed: 'JAM 23' is a new peach rootstock that is a *Prunus persica* (L.) Batsch.

Variety denomination: The new peach rootstock claimed is of the variety denominated 'JAM 23', *Prunus persica* (L.) Batsch.

BACKGROUND OF THE INVENTION

The present invention relates to the discovery of a new and distinct variety of peach botanically known as *Prunus persica* (L.) Batsch , and herein referred to as 'Jam 23', as herein described and illustrated. This new and distinct variety of peach tree is cold hardy and late blooming making it suitable for the reliable production of rootstock seeds with red leaf color, high levels of germination and cold hardiness. These seedlings can be used as cold-hardy red-leaf peach rootstocks or rootstocks for any *Prunus* species compatible with peach (*Prunus persica*) as a rootstock.

This new and distinct variety of peach originated at the Appalachian Fruit Research Station at Kearneysville, W.Va. where it was tested. 'Jam 23', is a seedling of KV981549 open pollinated. KV981549 is a hybrid of 'Bailey' x KV931777. KV931777 is a seedling of 'Bailey' x 14DR60. The parentage of 14DR60, a red leaf peach, is unknown. 'Jam 23' was selected as a single plant in 2001 from a group of 518 seedlings of the before said parents. Testing for 8 years has shown that the variety maintains vigorous growth, red color of leaves, late blooming, and heavy cropping. The description of 'Jam 23' contained herein is based from the same genotype, and not on any sexual progeny or other genotypes.

'JAM 23' peach rootstock is distinct from its parents in its combination of late blooming with high yield and flesh that is readily separated from the stone (freestone), with a high germination rate of its seeds (Table 1) and a high level of flower bud and wood cold hardiness, similar to the known cold hardy cultivar 'Bailey' (FIGS. 1, 2A-2B) favoring consistent production. These traits are combined with the distinct trait of homozygous inheritance of the red leaf trait, so that all progeny exhibit the red leaf trait (FIG. 3) allowing easy selection of rootstock growth in the nursery and in orchards. The cold hardy 'Bailey' parentage, the documented flower bud cold hardiness (FIG. 1) and wood cold hardiness of 'Jam 23' (FIG. 2A) and replicated tests indicate that seedlings of 'Jam 23' are cold hardy rootstock when used as rootstocks.

TABLE 1

Seed germination following cold chamber (4° C.) stratification from October 21 to March 29 with the stone (endocarp removed) or under natural field conditions with seed in stone planted in the field October 18 and evaluated for germination May 15. Cold chamber and field planting were each tests of 3 replications of 15 seeds per replication per cultivar.

| Cultivar | % Germination Cold Chamber Stratified Seed Removed from Stone | % Germination Seed in Stone |
|---|---|---|
| 'JAM 23' | 98 | 40 |
| 'Bailey' | 100 | 16 |
| 'Bounty' | 93 | 7 |
| 'Guardian' | 87 | 9 |
| 'TruGold' | 78 | 0 |

The new variety was propagated using vegetative propagation by bud-grafting on to seedling peach rootstock. Testing for 10 years has shown that said variety maintains late bloom, high fruit and seed productivity, and red leaf-color when bud-grafted onto standard rootstocks. Seedlings of 'JAM 23' produced through open-pollination of 'Jam 23' trees show a red coloration of leaves and young (non-woody) stems (FIG. 3).

BRIEF DESCRIPTIONS OF THE DRAWINGS

DETAILED DESCRIPTION OF THE INVENTION

Figure 1:
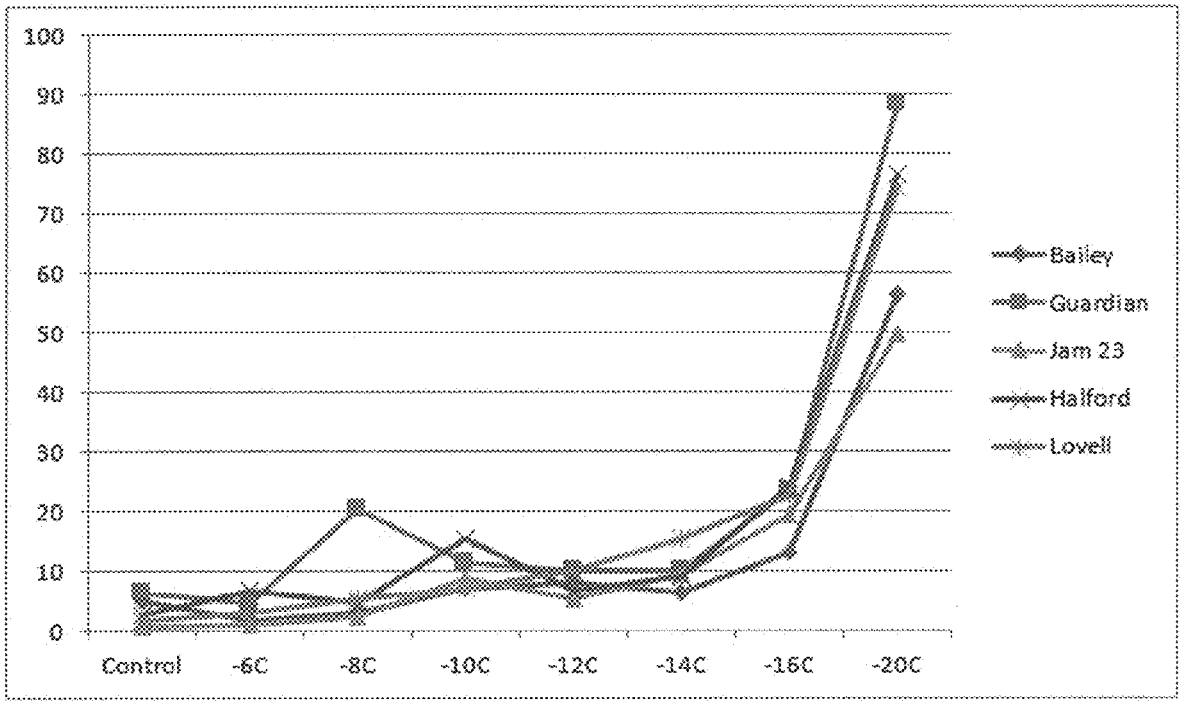
FIG. 1 is a graph showing Percentage of dead flower buds following exposure of budsticks containing dormant flower buds (Mar. 8, 2011) to controlled low temperatures in a freezing chamber with an average of 5 replications per genotype per temperature and an average of 114 buds sampled per genotype per temperature per replication.
Figure 2A:
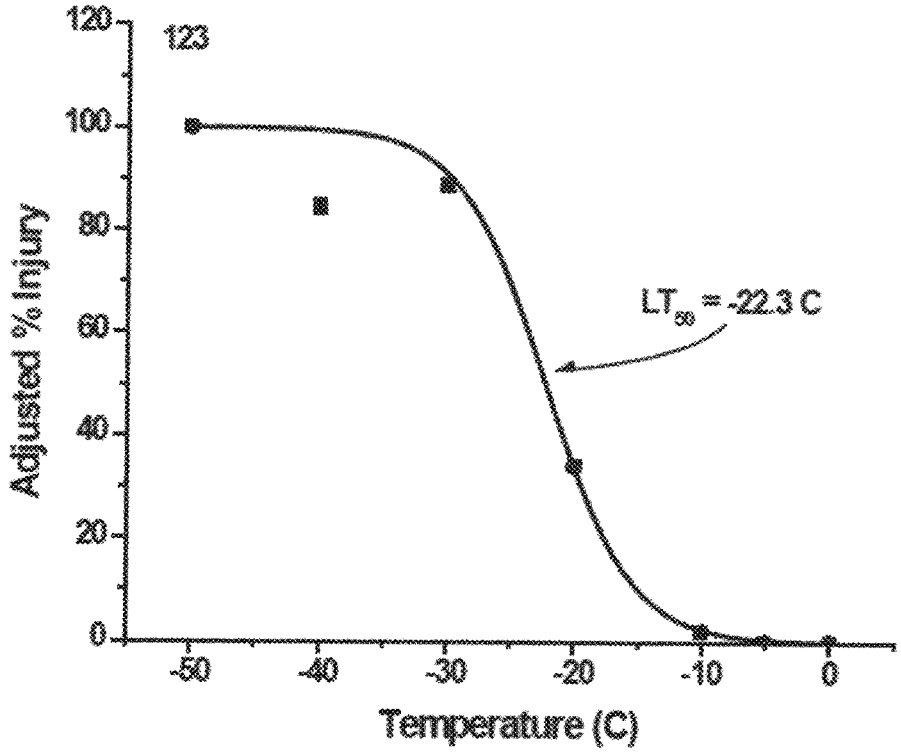
FIG. 2A is a graph showing lethal low temperature ($LT_{50}$) for survival of dormant shoots of 'Jam 23' (−22.3° C.), compared with commonly used peach rootstocks shown in FIGS. 2B and 2C, measured by ion leakage. Three replications per genotype per temperature (0, −5, −10, −20, −3−, −50° C.).
Figure 2B:
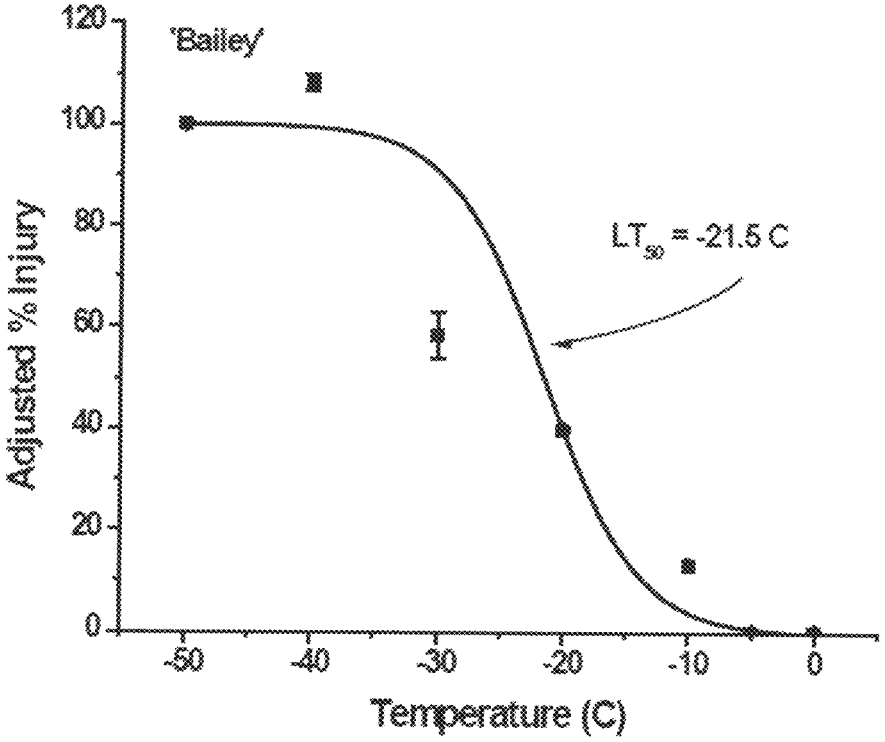
FIG. 2B is a graph showing lethal low temperature ($LT_{50}$) for survival of dormant shoots of the cold hardy rootstock 'Bailey' (−21.5° C.) measured by ion leakage. Three replications per genotype per temperature (0, −5, −10, −20, −3−, −50° C.).
Figure 2C:
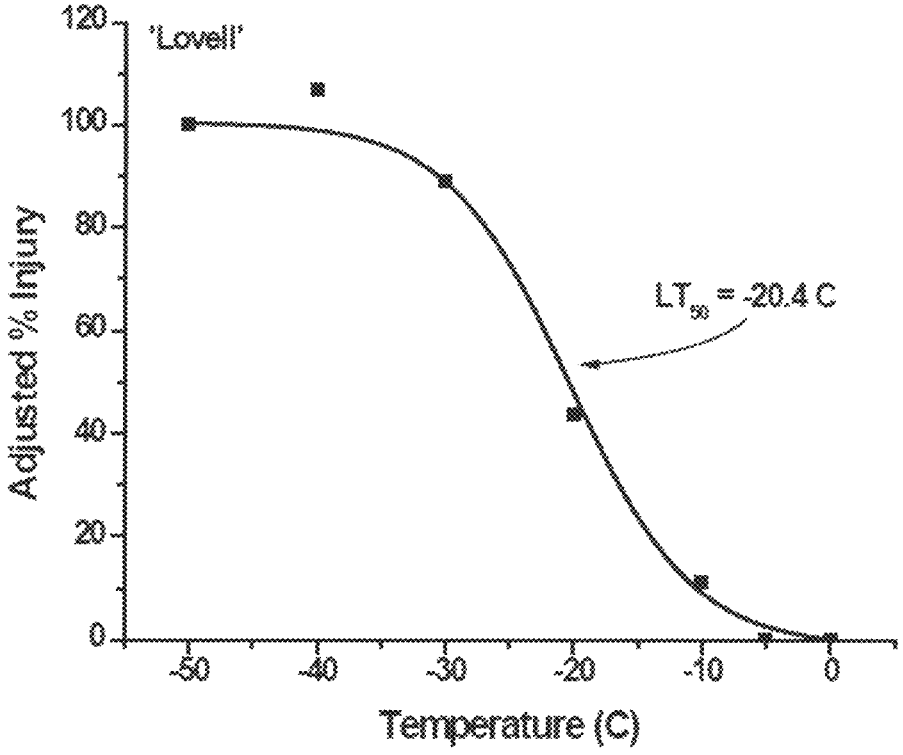
FIG. 2C is a graph showing lethal low temperature ($LT_{50}$) for survival of dormant shots of the standard rootstock 'Lovell' (−20.4° C.), measured by ion leakage. Three replications per genotype per temperature (0, −5, −10, −20, −3−, −50° C.).

'Jam 23' is unique in its combination of red coloration of leaves and young shoots, late bloom, cold hardiness of flower buds and shoots, high germination rate of seeds and the production of seedlings with red leaf and shoot coloration. The red leaf coloration serves to identify the rootstock in grafted trees. In the nursery following propagation by bud-grafting, if the grafted bud does not survive, the growth of the rootstock can be readily observed and these non-grafted trees can be eliminated. In the orchard or home garden, if the grafted scion variety dies at any stage in tree growth and the rootstock takes over the growth of the tree, which is not an uncommon occurrence, 'Jam 23' growth can readily be observed by the red leaf and shoot color and the tree can be eliminated or re-grafted to the desired variety. The late bloom and cold hardiness of 'Jam 23' as a rootstock seed source assures the production of rootstock seeds in years of extreme cold winters or in the case of late spring season frost events that would kill the flowers of earlier blooming trees and eliminate rootstock seed production. The high germination rate of 'Jam 23' seeds assures a good stock of graftable nursery rootstock. 'Jam 23' has been tested as selection KV010123 since 2009 as part of the NC-140 Regional Peach Rootstock Trial. Since 2009 these trials have indicated that tree survival, tree growth, fruit yield and fruit size of 'Redhaven' peach grafted to seedlings of 'Jam 23' is equal to, or in some locations in some years, superior to the experimental trial control rootstock 'Lovell'. 'Jam 23' rootstock induced a high fruit yield efficiency of the 'Redhaven' scion. Over all locations and years of the NC-140 trial to date 'Jam 23' has exerted a slight dwarfing effect on the growth of the 'Lovell' scion. This effect, which averaged 88% of growth of 'Redhaven' on the 'Lovell' control rootstock, was noted in many, but not all, test locations. Tree survival of 'Jam 23' in all locations was among the highest tested (Reighard et al 2015. Acta Horticulturae 1084: 225-232).

'Jam 23', was selected from a group of 518 seedlings of KV981549 that had been open pollinated. 'Jam 23' was selected for a high percentage of seed germination, high levels of flower bud and shoot cold hardiness, the homozygous state of the gene for red leaf and shoot coloration, and late bloom, through a series of tests as exemplified in Table 1 above and FIGS. 1, 2A-C, 3, 5A-C, and 6.

DETAILED BOTANICAL DESCRIPTION OF THE PLANT

The following horticultural description was developed from plant material of the new cultivar growing in Kearneysville, W.Va. Trees of 'Jam 23' were observed during the growing season 2015. At the time the trees were approximately 15 years old. Color definitions used throughout the following description are from The Royal Horticultural Society Colour Chart.

Tree:

*Size*.—Canopy 6.3 meters high from the ground at 10 years of age. Canopy 7.1 m in diameter at 10 years of age.

*Vigor*.—Vigorous — average seasonal growth of shoots 31.5 cm with a diameter of 3.98 mm.

*Growth*.—Spreading.

*Tree habit*.—Spreading.

*Productivity*.—High productivity.

*Bearing*.—Self-fertile, regular bearing.

*Type of bearing*.—On spurs and long shoots.

*Trunk*.—

*Size*.—Diameter 15.5 cm (measured at 20 cm above ground level).

*Color*.—Greyed green N189C.

Branches:

Scaffold branches:

*Size*.—Average diameter 6.35 cm.

*Bark color*.—Greyed green 197C to 197B.

*Scaffold branch lenticels color*.—Greyed green 197C to 197B. length — 4.9 mm. Width — 2.4 mm. Density — 22/cm$^2$.

Lateral branches:

*Bark color.*—Greyed brown 199A

*Lenticels.*—Color — greyed orange N167C. Length — 1.4 mm. Width — 0.7 mm. Density — 6.5/cm$^2$. Angle from the supporting limb — 50.6°.

Leaves: Leaves are lanceolate, apex is acuminate, base is cuneate margin is crenate.

*Color.*—Adaxial — mature leaves are green group 137B to 137C, older leaves become yellow-green 146A abaxial — yellow green 147B. mid-rib — yellow green 144D with over-color of greyed purple 187C to 185D depending on age and light exposure.

*Emerging young leaf color.*—Greyed purple 187A-187B.

Petiole: Petiole is longitudinally grooved, color is yellow-green 144C tinged with greyed purple 184A.

*Average length.*—8.25 mm.

*Average width.*—1.47 mm.

*Average thickness.*—1.46 mm.

*Stipule length.*—10.9 mm.

Blade:

*Average length.*—14.1 cm.

*Average width.*—4.0 cm.

*Average thickness.*—0.13 mm.

*Leaf blade shape in cross-section.*—Flat.

*Leaf blade angle at apex.*—45°.

*Leaf blade angle at base.*—70.6°.

Leaf glands: Leaf glands are round, located on petiole and/or base of leaf blade. Color is yellow-green 151B.

*Average number.*—2.

*Average diameter.*—0.78 mm.

Vegetative buds:

*Position of vegetative bud in relation to one-year-old shoot.*—Slightly held out.

*Spur length.*—16.3 mm.

*Vegetative bud size.*—Length 2.6 mm, width 1.1 mm.

*Vegetative bud shape of apex.*—Acute.

*Time of leaf bud burst.*—Averages April 13.

Flower buds and flowers:

Flower buds:

*Color.*—Grey 201C over brown N200A.

*Average length.*—4.2 mm.

*Average width.*—2.3 mm.

*Average # of buds per node.*—0.9.

*Average # of buds per cm.*—0.5.

*Bud scale color.*—Adaxial — greyed-orange 166B streaked with greyed-orange 175B. Abaxial — tomentose, brown N200D, over greyed orange 166B.

Figure 3:
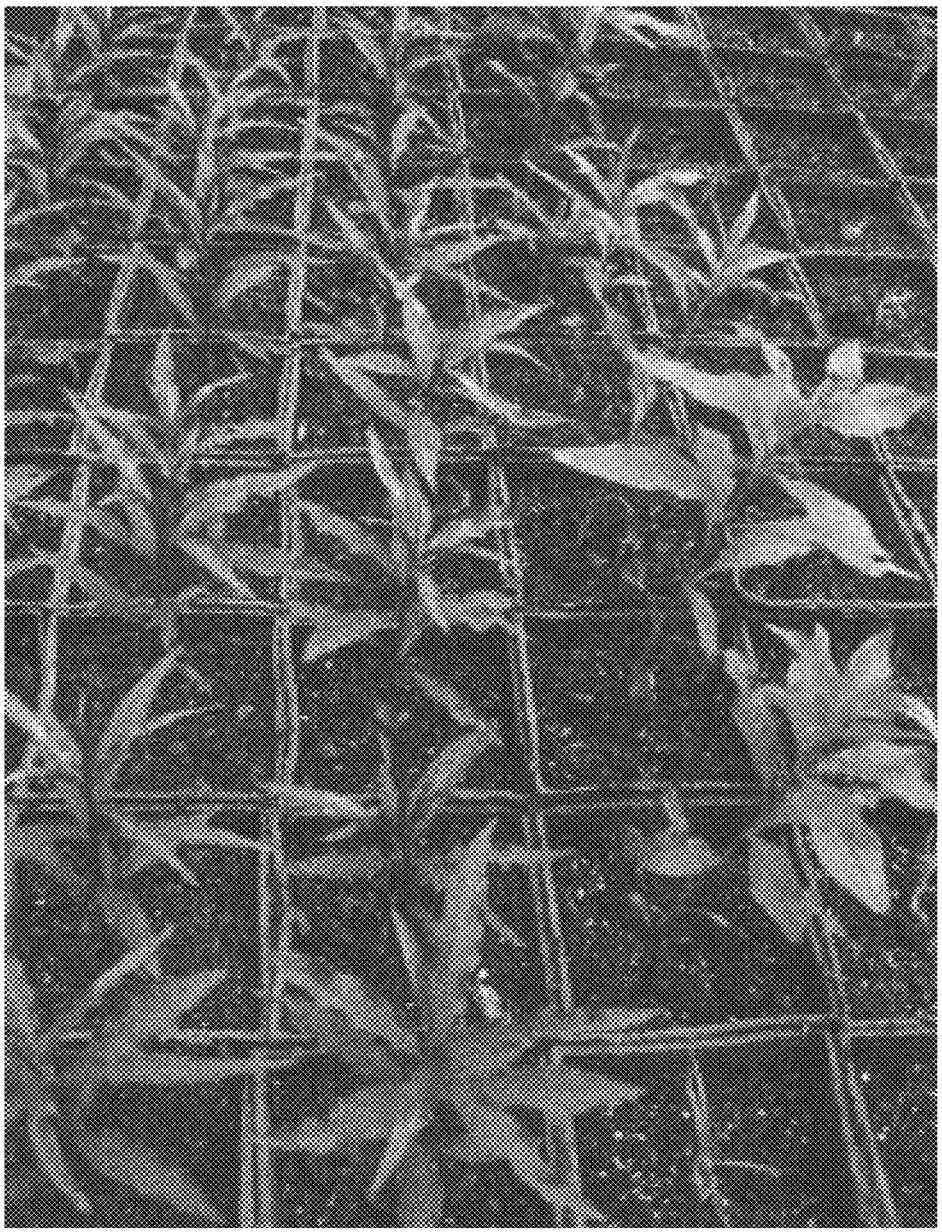
FIG. 3 is a photograph of seedlings of open pollination of 'Jam 23' on left side of photograph and green leaf seedlings of 'Bailey' on the right side of the photograph.

*Flower bud cold hardiness.*—Similar to that of 'Bailey' (see FIG. 3).

*Time of flowering.*—Averages April 10.

Flowers:

*Flower type.*—Rosette.

Petal:

*Color.*—Red purple 62C, aging to N66D with stalk and veins red purple 64B.

*Average petal length.*—18.2 mm.

*Average petal width.*—14.1 mm.

*Petal shape.*—Medium ovate.

*Average flower diameter.*—31.2 mm.

*Arrangement of petals.*—Touching.

*Average number of petals.*—5.

Stamen:

Anther:

*Color.*—Red 53C.

*Average anther length.*—0.98 mm.

*Average anther width.*—0.84 mm.

*Average number/flower.*—39.6.

*Position relative to petals.*—At same level.

Filament:

*Average filament length.*—11.5 mm.

*Filament color.*—Red-purple 69B aging to red-purple 64A to 64B.

Pistil:

*Overall average length of pistil.*—20 mm.

Stigma:

*Color.*—Yellow-green 154C.

*Average diameter.*—0.76 mm.

*Position relative to petals.*—At same level.

Style:

*Color.*—Red 53B.

*Average diameter.*—0.36 mm.

Ovary:

*Average height.*—3.5 mm.

*Average diameter.*—2.4 mm.

*Color.*—Hairs — white 155B. Ovary — yellow-green 145A.

Hypanthium:

*Hypanthium diameter.*—6.0 mm.

*Hypanthium height.*—7.23 mm.

*Color.*—Abaxial — greyed purple 183D. Adaxial — yellow-green 151A tinged with greyed oranged 172C.

Calyx (sepals):

*Average sepal length.*—4.7 mm.

*Average sepal width.*—4.1 mm.

*Color.*—Abaxial — greyed purple 183D. Adaxial — greyed purple 185C.

Pollen:

*Color.*—Yellow 13A. Pollen is abundant, fertile.

Fruit:

*Timing of fruit maturity.*—August 14-24, average August 20; fruit harvested at soft ripe.

*Average weight.*—6.7 g.

*Average length.*—41.4 mm.

*Average width.*—40.5 mm.

*Average thickness.*—39.0 mm.

*Flesh thickness.*—13.1 mm.

*Depth of fruit suture.*—0.5 mm.

*Epidermis ground color.*—Green-white 157A to 155B.

*Overcolor.*—Greyed purple 184C to 184D, some areas of 183B.

*Relative area of fruit overcolor.*—90%.

*Pattern of fruit overcolor.*—Mostly solid flush, occasionally marbled.

*Pubescence.*—Yellow white 158A.

*Flesh color.*—White 155C stained with greyed purple 185B to 185A. No bloom on fruit of skin.

*Adherence of skin to flesh.*—Moderate.

*Number of fruit lenticels.*—None.

*Pit cavity color.*—White 155C stained with greyed purple 185B to 185A.

*Pit cavity depth.*—8.1 mm.

*Pit cavity width.*—10.4×13.2 mm.

*Penduncle length.*—4.3 mm.

*Penduncle width.*—3.6 mm. Slightly elongated in suture plane.

*Average length.*—27.7 mm.
*Average width.*—21.0 mm.
*Average diameter.*—14.7 mm.
*Shape of fruit base.*—Depressed.
*Shape of fruit apex.*—Pointed.
*Fruit shape in lateral view.*—Elliptical.
*Depth of fruit stalk cavity.*—3.2 mm.
*Fruit firmness.*—Soft ripe at harvest, 10.67 N.
*Fruit juiciness.*—Fruit mealy, no appreciable amount of juice by conventional means.
*Fruit sweetness.*—11.5° Brix.
*Amount of fruit fiber.*—High, many small fibers, flavor astringent.

Figure 4:
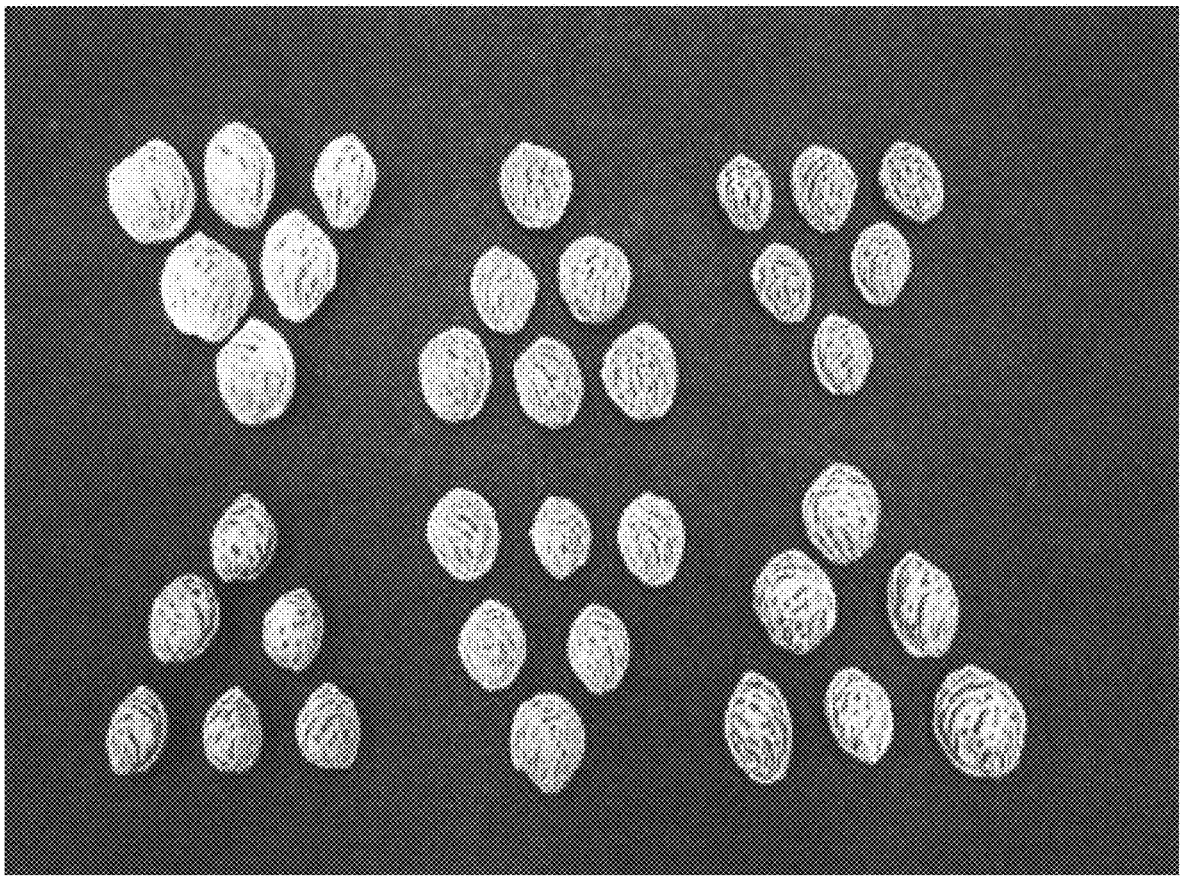
FIG. 4 is a photograph showing seeds of 'Bounty' (upper left), 'Jam 23' (upper middle), 'Bailey' (upper right), 'Guardian' (lower left), Seedling KV010127 (lower middle), 'TruGold' (lower right).
Figure 5A:
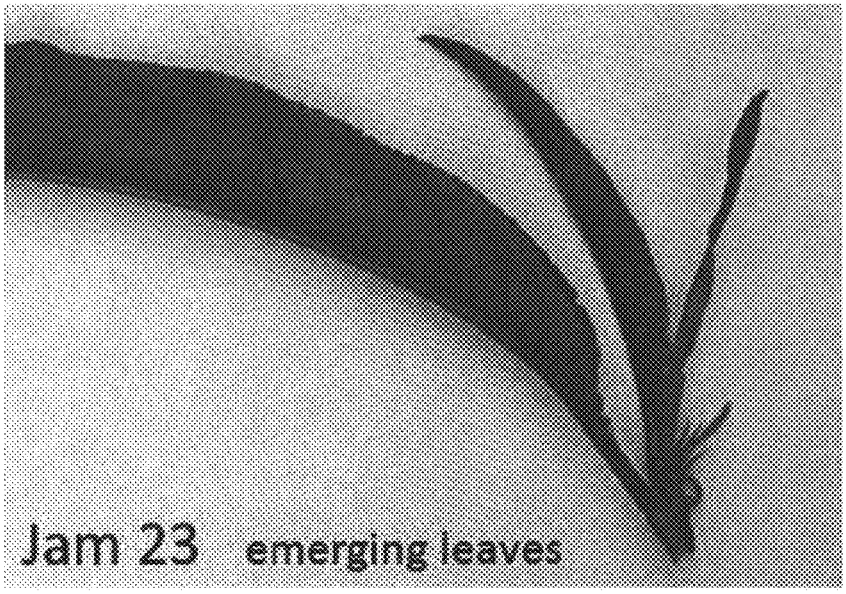
FIG. 5A is a photograph of emerging leaf color of 'Jam 23'.
Figure 5B:
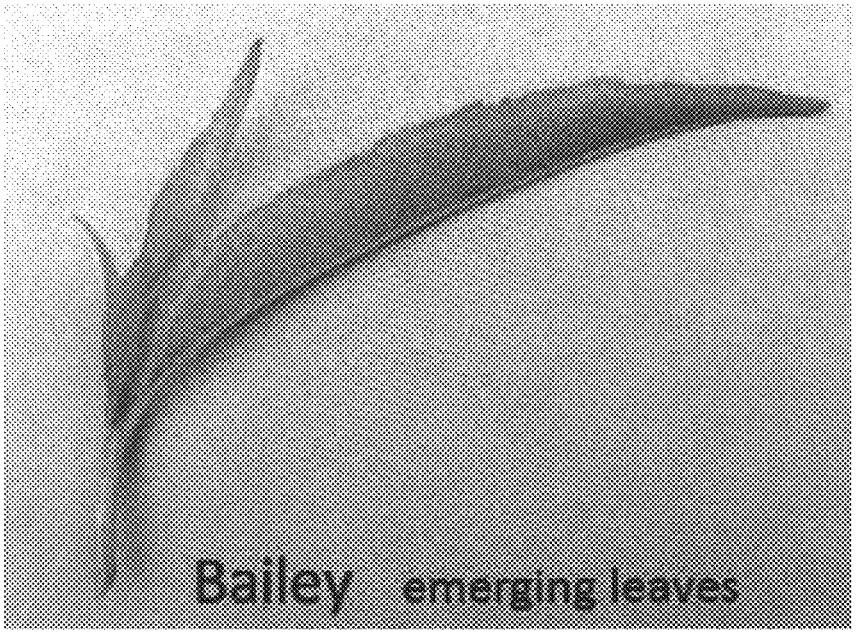
FIG. 5B is a photograph showing emerging leaves of 'Bailey' rootstock.
Figure 5C:
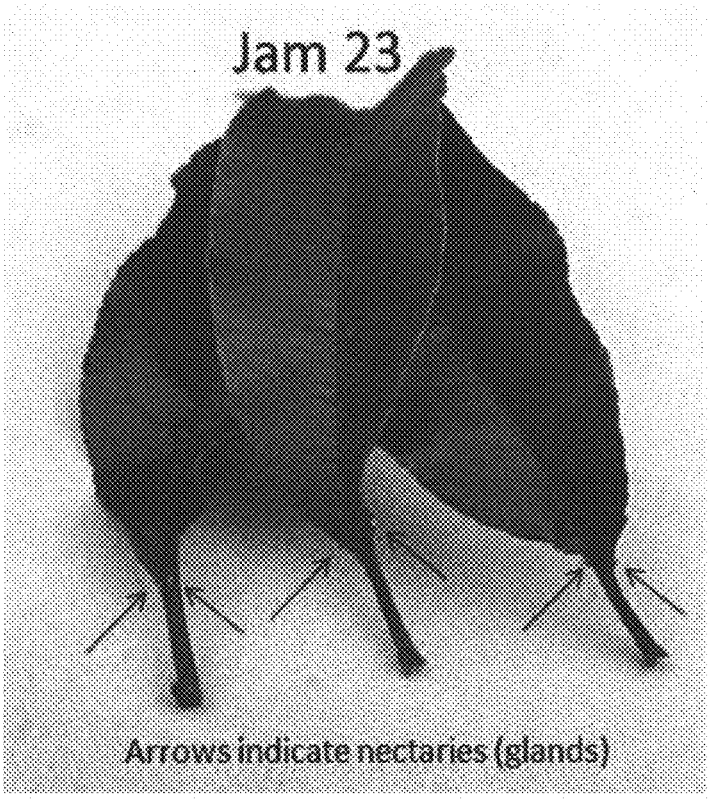
FIG. 5C is a photograph showing Nectaries (glands) of 'Jam 23'
Figure 5D:
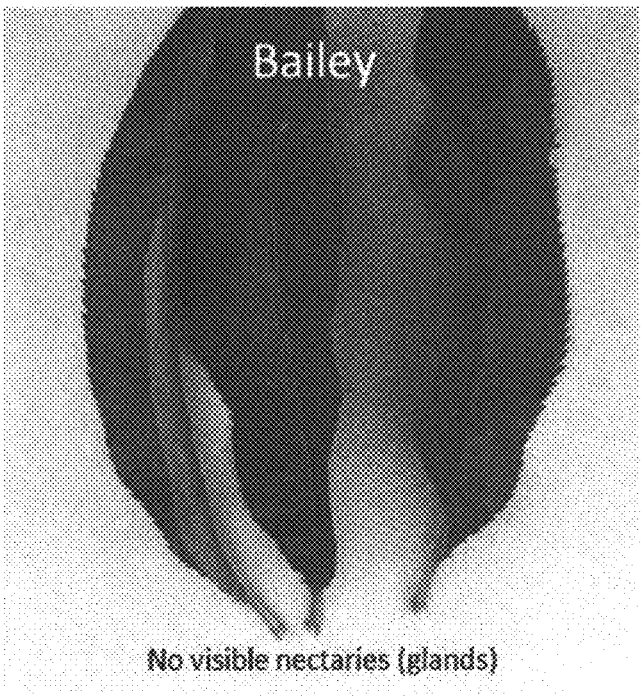
FIG. 5D is a photograph showing leaves from 'Bailey' rootstock showing no visible nectaries.
Figure 6:
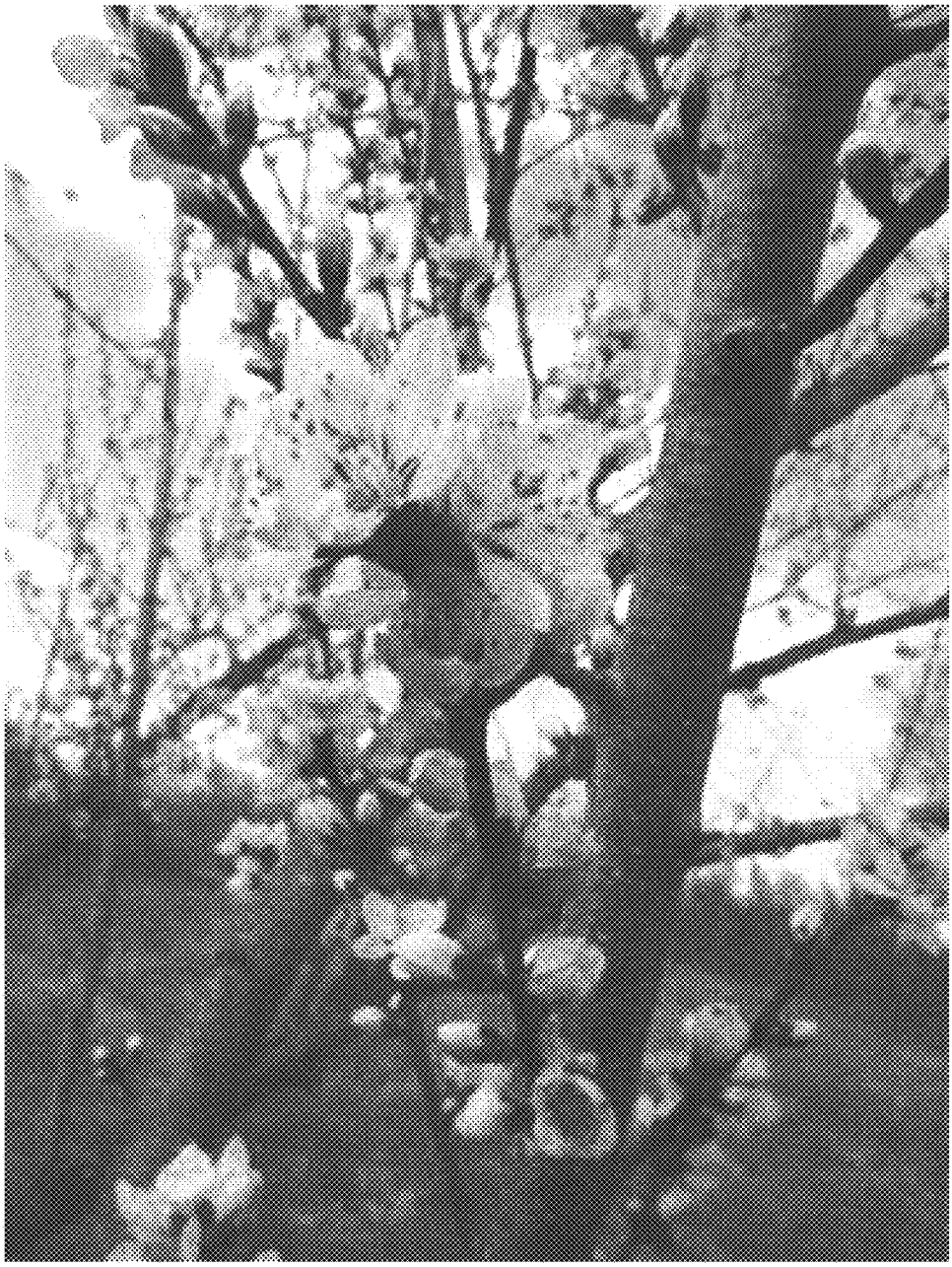
FIG. 6 is a photograph showing the flower color of 'Jam 23'.
Figure 7A:
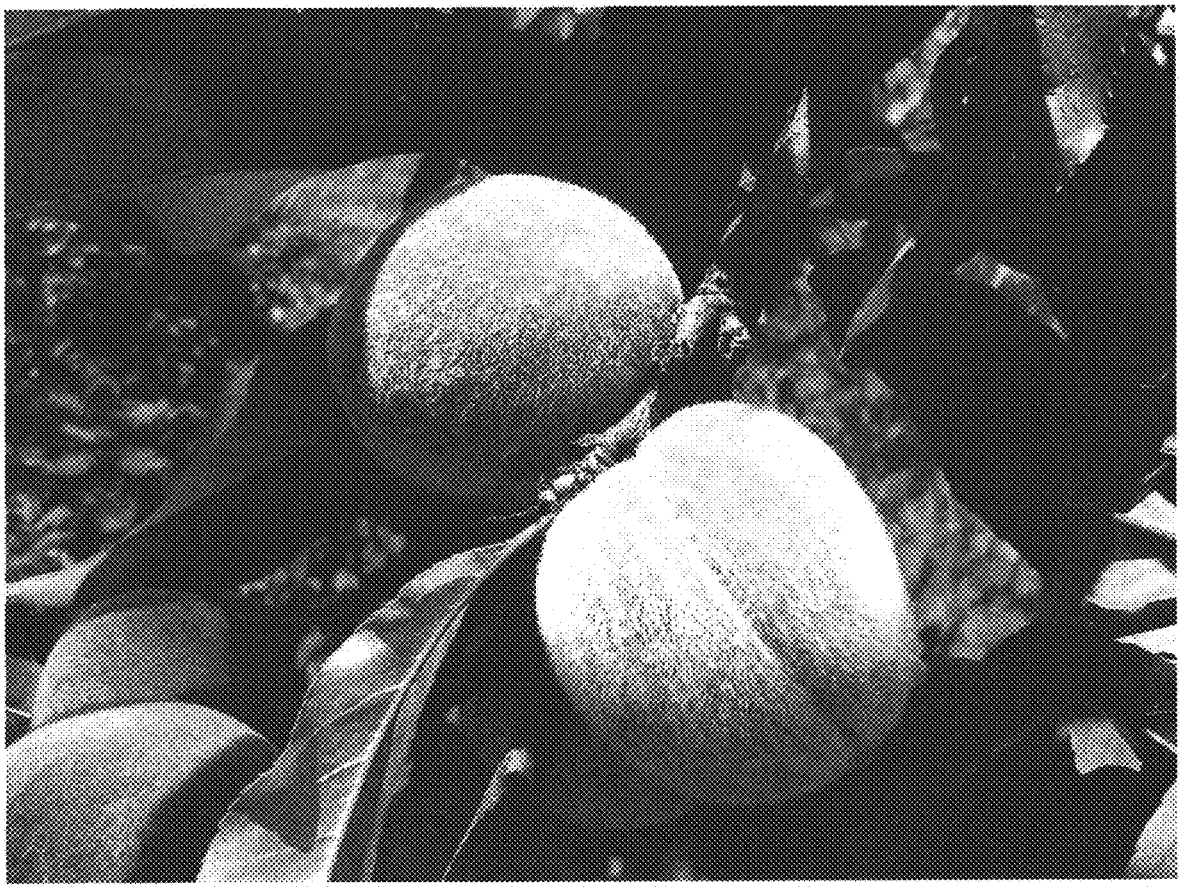
FIG. 7A is a photograph of fruit of 'Jam 23' on a spur.
Figure 7B:
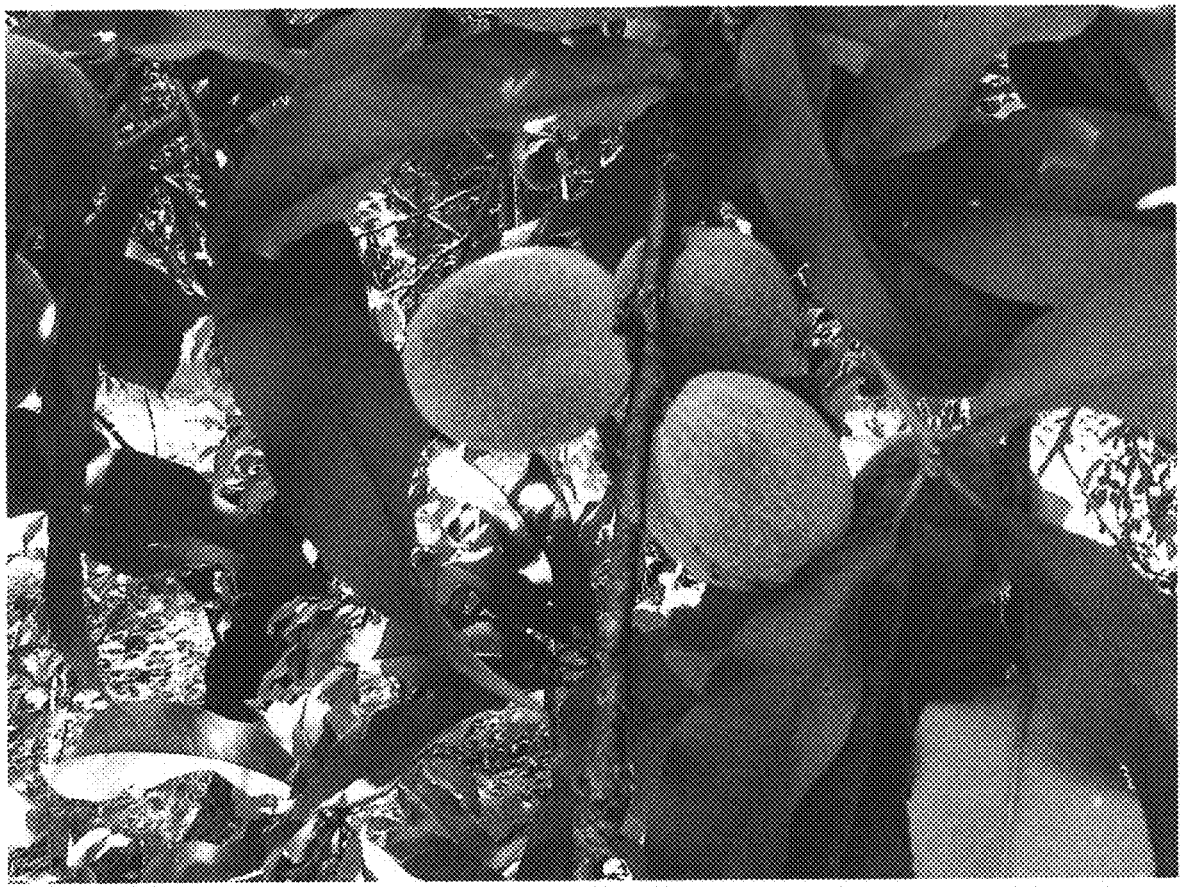
FIG. 7B is a photograph of fruit of 'Jam 23' on a long shoot.
Figure 8:
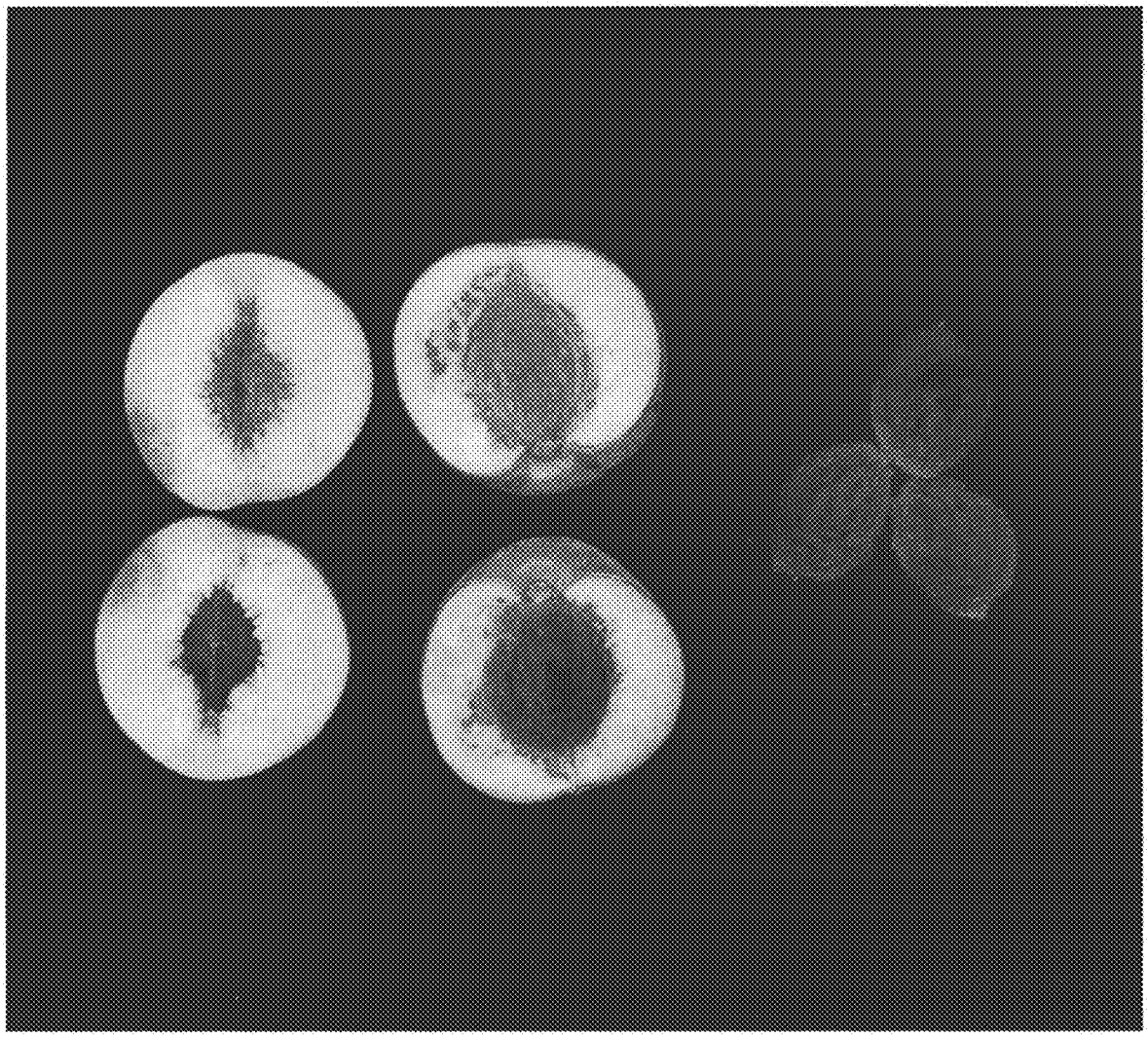
FIG. 8 is a photograph showing cross-sectional views of fruit of 'Jam 23' with pits of 'Jam 23' to one side.

Stone (FIG. 4):

*Average weight.*—3.2 g.
*Average length.*—28.7 mm.
*Average width.*—21.1 mm.
*Average thickness.*—14.2 mm.
*Freestone,* (*stone readily separates from the surrounding flesh*).—Ovoid shape, pointed, pits round to elongated.
*Stone color.*—Greyed orange 177B to 177A. Stained with greyed purple 185B when wet.
*Kernel cavity color.*—Greyed orange 165D to 165C.
*Stone shape in lateral view.*—Obovate.
*Stone shape in ventral view.*—Elliptical.
*Stone shape in basal view.*—Elliptical.
*Stone symmetry in lateral view.*—Asymmetrical.
*Stone texture of lateral surfaces.*—Rough.
*Stone relief of surface.*—Pits and grooves.
*Stone width of stalk end.*—2.9 mm.

Kernel:

*Average weight.*—0.34 g.
*Average length.*—15.7 mm.
*Average width.*—9.8 mm.
*Average thickness.*—4.6 mm.
*Average number kernels.*—1.04.
*Kernel color.*—Greyed orange 164B with vein of 164A. Seed germination was high (see Table 1).

We claim:

1. We claim a new and distinct variety of red leaf peach tree, 'Jam 23', for the production of cold-hardy red leaf *Prunus* rootstocks with high levels of germination as illustrated and shown herein.

* * * * *

'Jam 23'

'Bailey'

'Lovell'